(12) United States Patent
Eklin et al.

(10) Patent No.: US 11,719,638 B2
(45) Date of Patent: Aug. 8, 2023

(54) METHOD OF ANALYZING SAMPLES, ANALYZING DEVICE AND COMPUTER PROGRAM

(71) Applicant: Life Technologies Holdings PTE LTD, Singapore (SG)

(72) Inventors: Katja Eklin, Espoo (FI); Adyary Fallarero, Vantaa (FI); Tommi Suvanto, Espoo (FI); Marika J. Raitio, Helsinki (FI)

(73) Assignee: Life Technologies Holdings PTE LTD, Singapore (SG)

( * ) Notice: Subject to any disclaimer, the term of this patent is extended or adjusted under 35 U.S.C. 154(b) by 485 days.

(21) Appl. No.: 16/625,467

(22) PCT Filed: Jun. 27, 2018

(86) PCT No.: PCT/FI2018/050511
§ 371 (c)(1),
(2) Date: Dec. 20, 2019

(87) PCT Pub. No.: WO2019/002688
PCT Pub. Date: Jan. 3, 2019

(65) Prior Publication Data
US 2021/0148822 A1 May 20, 2021

(30) Foreign Application Priority Data
Jun. 27, 2017 (FI) .................................. 20175607

(51) Int. Cl.
*G01N 21/25* (2006.01)
*G01N 21/64* (2006.01)
*C12Q 1/686* (2018.01)

(52) U.S. Cl.
CPC ......... *G01N 21/6452* (2013.01); *C12Q 1/686* (2013.01); *G01N 21/253* (2013.01);
(Continued)

(58) Field of Classification Search
CPC ............ G01N 21/6452; G01N 21/253; G01N 2201/04; G01N 2201/0461; G01N 2201/0469; C12Q 1/686
See application file for complete search history.

(56) References Cited

U.S. PATENT DOCUMENTS 6,372,183 B1  4/2002  Akong et al.
6,406,913 B1  6/2002  Ullman et al.
(Continued)

FOREIGN PATENT DOCUMENTS

CN  101283241 A  10/2008
CN  104422678 A  3/2015
(Continued)

OTHER PUBLICATIONS

International Search Report and Written Opinion dated Sep. 27, 2018, issued in PCT Application No. PCT/FI2018/050511, filed Jun. 27, 2018.
(Continued)

*Primary Examiner* — Violeta A Prieto
(74) *Attorney, Agent, or Firm* — BakerHostetler

(57) ABSTRACT

The method of analyzing one or more samples arranged in sample receptacles of a platform that is configured to receive a plurality of separate samples includes the steps of measuring electromagnetic radiation transmitted or emitted by each sample, repeating the measurement a plurality of times at predetermined intervals, on the basis of each measurement, forming a result matrix comprising a plurality of cells, each cell of the result matrix corresponding to a sample receptacle of the plat-form, wherein a measurement value of each sample is used as an input for determining the visual properties of the respective cell in the result matrix, and displaying the results as consecutive matrixes in respect of time.

19 Claims, 10 Drawing Sheets

(52) U.S. Cl.
CPC . *G01N 2201/04* (2013.01); *G01N 2201/0461* (2013.01); *G01N 2201/0469* (2013.01)

(56) References Cited

U.S. PATENT DOCUMENTS

| | | | |
|---|---|---|---|
| 6,466,316 B2 * | 10/2002 | Modlin | G01N 21/253 |
| | | | 356/417 |
| 2001/0003044 A1 | 6/2001 | Moldin et al. | |
| 2004/0202577 A1 | 10/2004 | McNeil et al. | |
| 2005/0133724 A1 | 6/2005 | Hsieh et al. | |
| 2006/0227320 A1 | 10/2006 | Eiichi et al. | |
| 2007/0037135 A1 | 2/2007 | Barnes et al. | |
| 2008/0191149 A1 * | 8/2008 | Zimenkov | G01J 3/443 |
| | | | 250/492.1 |
| 2008/0263468 A1 | 10/2008 | Cappione et al. | |
| 2013/0203173 A1 | 8/2013 | Tikanoja et al. | |
| 2013/0271593 A1 | 10/2013 | Tsujimoto et al. | |
| 2014/0320513 A1 * | 10/2014 | Ogi | G06V 20/695 |
| | | | 345/581 |
| 2015/0152941 A1 | 6/2015 | Sekiguchi et al. | |
| 2016/0018429 A1 | 1/2016 | Florian et al. | |
| 2016/0064699 A1 | 3/2016 | Park et al. | |
| 2016/0313255 A1 | 10/2016 | Pardee et al. | |
| 2017/0298436 A1 * | 10/2017 | Kaseniit | G16H 10/40 |
| 2018/0096498 A1 * | 4/2018 | Hartmann | G06T 11/206 |
| 2018/0196193 A1 * | 7/2018 | Ozcan | G01N 21/253 |

FOREIGN PATENT DOCUMENTS

| | | |
|---|---|---|
| CN | 105247035 A | 1/2016 |
| JP | H10-507518 A | 7/1998 |
| JP | 2004-286666 A | 10/2004 |
| JP | 2010-527469 A | 8/2010 |
| JP | 2013-152452 A | 8/2013 |
| JP | 2017-067605 A | 4/2017 |
| WO | 2013/181347 A1 | 12/2013 |
| WO | 2016/065115 A1 | 4/2016 |
| WO | 2016/080187 A1 | 5/2016 |
| WO | 2016/205736 A1 | 12/2016 |

OTHER PUBLICATIONS

Finnish Search Report dated Mar. 6, 2018, issued in Finnish Application No. 20175607.
Chinese Office Action dated Apr. 24, 2022, issued in Chinese Application No. 201880042976.1.
Japanese Office Action dated May 30, 2022, issued in Japanese Application No. 2019-572517.

* cited by examiner

METHOD OF ANALYZING SAMPLES, ANALYZING DEVICE AND COMPUTER PROGRAM

TECHNICAL FIELD OF THE INVENTION

The present invention relates to a method of analyzing one or more samples arranged in sample receptacles of a platform that is configured to receive a plurality of samples in accordance with claim 1. The invention also concerns an analyzing device and a computer program for operating an analyzing device as defined in the other independent claims.

BACKGROUND OF THE INVENTION

A microplate (also called e.g. as a microtiter plate, microwell plate, multiwell plate or multiwell) is a flat plate comprising a plurality of wells, i.e. cavities that are arranged in rows and columns. The wells are configured to receive samples and function as small test tubes. A typical microplate comprises 6, 24, 96, 384 or 1536 wells, although also larger microplates exist. The wells are arranged in a rectangular matrix, where the ratio between the sides is typically 2:3. The samples are usually liquid, but microplates can also be used for example for samples that are in the form of powder. The microplates are typically made of a plastic material. The plates may be clear, opaque or colored, for example white or black. However, all microplates are not necessarily suitable for all applications.

Microplates are widely used in life sciences. Samples are placed in the wells of the microplates and analyzed with a microplate reader. A microplate reader can detect biological, chemical or physical events of the samples in the microplate. The microplate readers can be based on different phenomena, such as absorbance or luminescence.

Absorbance detection can be used for many different kinds of assays. In absorbance detection, the absorbance (optical density) of a sample is measured using a spectrophotometer. The change in absorbance correlates with some biological, chemical or physical change in the sample. Absorbance-based assays are popular, among other reasons, because often there is also a visible change of color in the sample.

Fluorescence is a form of luminescence and based on emission of light (a photon) by a substance that has absorbed light or other electromagnetic radiation. Absorbance of energy excites an orbital electron of a molecule to higher electronic states and relaxation to ground state emits a photon. In fluorescence measurements the sample is illuminated with an excitation light absorbed by the sample and light emitted by the sample is measured by a detector. In other assays, luminescence emission is created for instance as a result of a chemical reaction in the sample (chemiluminescence).

Fluorophores absorb light energy at one wavelength and, in response, re-emit light energy at another, longer wavelength. Each fluorophore has a distinctive range of wavelengths at which it absorbs light and another distinct range of wavelengths at which it emits light. This property enables their use for specific detection of biological products by analytical instruments and techniques.

Microplates can be used both for endpoint and kinetic assays. In endpoint assays, each sample is analyzed by a single measurement, which is carried out after allowing a certain reaction to take place in the samples. In kinetic studies a certain measurement is repeated at predetermined time intervals. With kinetic studies, a large amount of data can be gathered. Also the kinetic studies can be based on different phenomena, such as absorbance, fluorescence or luminescence. The results of kinetic studies are typically displayed as curves, where measurement signals are presented as a function of time. Especially in the case of larger microplates, the behavior of individual samples is difficult to interpret.

Similar problems arise also in other analysis techniques, such as real-time Polymerase Chain Reaction (PCR). PCR is used for generating a large number of copies of a particular DNA sequence. The progress of the process can be monitored by utilizing fluorescence. Samples can be arranged in liquid containing receptacles or cavities in an array or microplate format, and excitation energy in the form of electromagnetic radiation is directed at the samples. Electromagnetic radiation emitted by the samples is monitored by means of a detector.

SUMMARY OF THE INVENTION

An object of the present invention is to provide an improved method of analyzing one or more samples arranged in sample receptacles of a platform that is configured to receive a plurality of separate samples. The characterizing features of the method according to the invention are given in claim 1. Another object of the invention is to provide an improved analyzing device. Still another object of the invention is to provide an improved computer program for operating an analyzing device.

The method according to the invention comprises the steps of measuring electromagnetic radiation transmitted or emitted by each sample, repeating the measurement a plurality of times at predetermined intervals, on the basis of each measurement, forming a result matrix comprising a plurality of cells, each cell of the result matrix corresponding to a sample receptacle of the platform, wherein a measurement value of each sample is used as an input for determining the visual properties of the respective cell in the result matrix, and displaying the results as consecutive matrixes in respect of time.

With the method according to the invention, the results of kinetic assays can be interpreted more reliably. This is particularly important and useful when a large number of samples are analyzed. For instance, if microplates with a large number of wells, such as 384 wells or more, are used as sample platforms, the results cannot be easily shown as numerical values in the limited space of a user interface. The use of measurement values as inputs for determining the visual properties of the result matrixes allows larger amounts of data to be shown on a display at a time and a user of an analyzing device can quickly detect whether the results look reliable and can either repeat the analysis with corrected parameters or move to analyzing a next set of samples.

The sample receptacles can be open holes or closed cavities. They can be either integral parts of the platform, such as wells of a microplate, or separate vessels inserted into the platform, such as test tubes in a rack.

According to an embodiment of the invention, in the measurement step absorbance values of the samples are measured.

According to an embodiment of the invention, the method comprises the step of illuminating the samples using electromagnetic radiation having a bandwidth of at most 20 nm around a set wavelength falling within the wavelength range of 380 nm-750 nm.

According to an embodiment of the invention, the set wavelength is used as a further input for determining the visual properties of the cells. By using the set wavelength as an input for determining the visual properties of the cells, the result matrixes can be configured to better resemble the set of samples in a microplate or other platform and the user of the method can more easily interpret the results.

According to an embodiment of the invention, the color of each cell is selected so that the color corresponds to the color of the sample as perceived by the human eye. The color of each cell is thus selected to be the complementary color of the color corresponding to the set wavelength.

According to an embodiment of the invention, the amount or intensity of luminescence of the samples is measured.

According to an embodiment of the invention, the amount or intensity of fluorescence of the samples is measured.

According to an embodiment of the invention, the wavelength of the electromagnetic radiation emitted by the samples is used as a further input for determining the visual properties of the cells.

According to an embodiment of the invention, the color of each cell is selected so that the wavelength corresponding to the color of the cell is within 20 nm from the wavelength of the electromagnetic radiation emitted by the samples. The color of each cell can correspond to the color of the electromagnetic radiation emitted by the samples. By using the emission wavelength as an input for determining the visual properties of the cells, the result matrixes can be configured to better mimic the behavior of fluorophores in the set of the samples in the microplate or other platform and the user of the method can more easily interpret the results.

According to an embodiment of the invention, the transparency of each cell is determined on the basis of a measurement value of the respective sample.

Since the transparency of each cell correlates with the measurement value, the user can easily spot the interesting samples.

According to an embodiment of the invention, the transparencies of the cells are set by means of alpha blending and the alpha channel values of the cells have a positive correlation with the measurement values. The samples with higher measurement values are thus shown as less transparent cells on the display.

According to an embodiment of the invention, the measurement values are used for creating a video file illustrating the change of the measurement values between consecutive measurements.

The platform can be a microplate and the sample receptacles wells of the microplate.

The analyzing device according to the invention is configured to implement the method defined above. The device can be, for instance, a microplate reader or a PCR analyzer.

The computer program according to the invention comprises instructions which, when the program is executed by a computer, cause an analyzing device, such as a microplate reader or PCR analyzer, to carry out the method defined above.

BRIEF DESCRIPTION OF THE DRAWINGS

Embodiments of the invention are described below in more detail with reference to the accompanying drawings, in which.

DESCRIPTION OF EMBODIMENTS OF THE INVENTION

Figure 1:
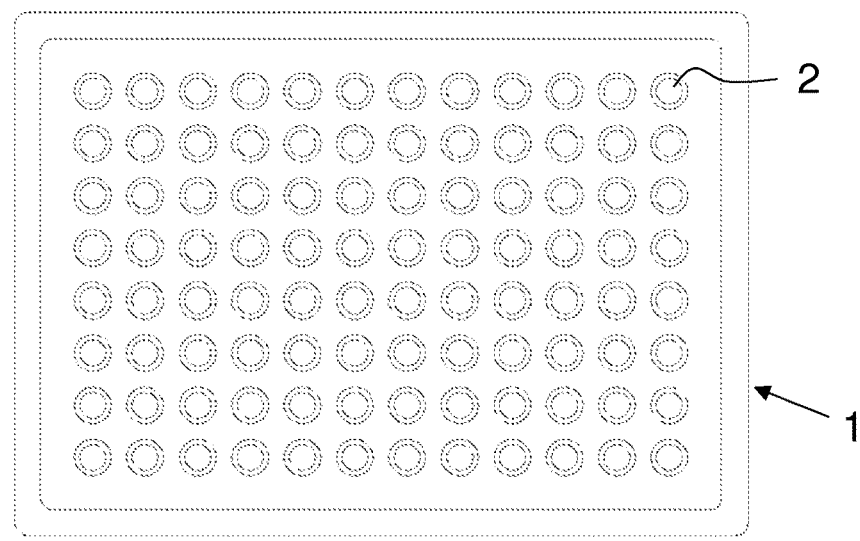
FIG. 1 shows an example of a microplate.

Microplates are widely used in life sciences. FIG. 1 shows an example of a microplate 1. The microplate comprises a plurality of wells 2, i.e. cavities that are arranged in rows and columns. The wells 2 are configured to receive samples and function as small test tubes. The bottoms of the wells can be flat, round or v-shaped. The microplate 1 of FIG. 1 comprises 96 wells arranged in 8 rows and 12 columns. Other common sizes of microplates 1 comprise 6, 24, 384 or 1536 wells, but also other sizes are available. The ratio between the sides is typically 2:3. The samples are usually liquid, but microplates 1 can also be used for samples that are in the form of powder or in other forms.

The samples placed in the wells 2 of a microplate 1 can be analyzed using a microplate reader. A microplate reader can detect biological, chemical or physical events of the samples in the microplate 1. The microplate readers can be based on different phenomena, such as absorbance or luminescence. Absorbance detection is a common technology, which can be used for many different kinds of assays. In absorbance detection, the absorbance (optical density) of a sample is measured using a spectrophotometer. The sample is often colored. A change in color hue or intensity in a sample correlates with some biological, chemical or physical change in the sample. Absorbance-based assays are popular because of the visible change in the color of a sample. In the following, the use of a microplate reader for absorbance measurements is described in more detail. However, the present invention is also suitable for assays that are based on, for instance, fluorescence or other forms of luminescence. Different sample measuring methods based on photoluminescence are known from prior art, wherein emission of light from the sample is obtained with an excitation of light into the sample. When the light emitted by the sample is measured, different properties of the sample can be determined.

Figure 2:
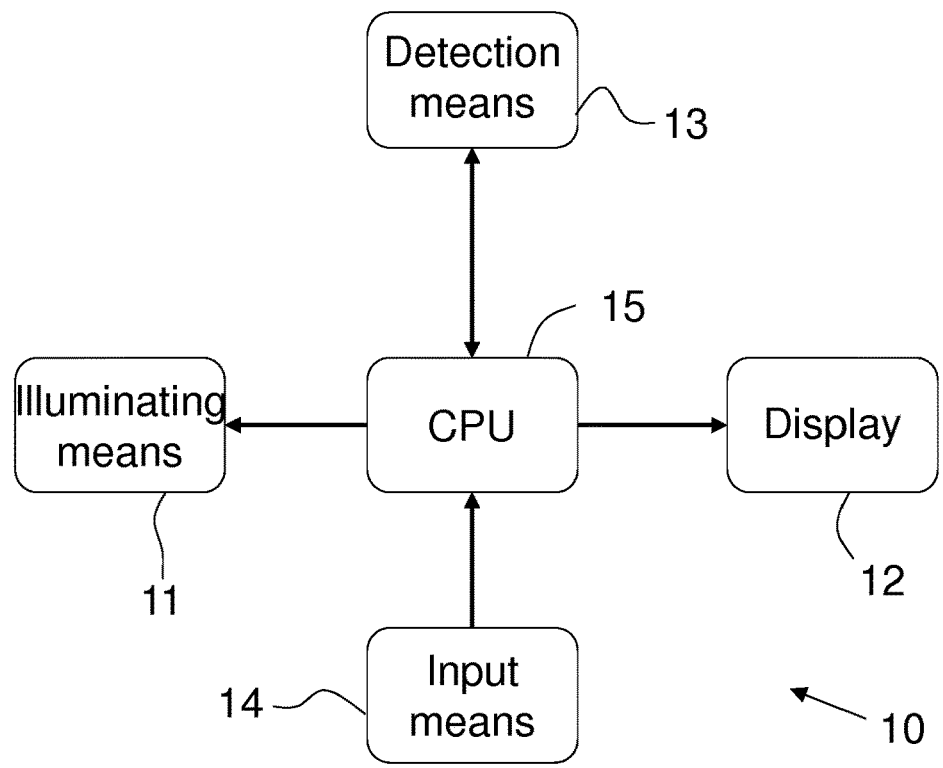
FIG. 2 shows the main elements of a microplate reader.

FIG. 2 shows schematically the main components of a typical microplate reader 10. The microplate reader 10 can be configured for certain types of assays, such as absorbance-based assays, luminescence-based assays or fluorescence-based assays. The microplate reader 10 could be, for instance, a spectrofluorometer or a multi-mode device, which is suitable for different purposes, such as for all the above-mentioned assays. The microplate reader 10 could also be used for example for AlphaScreen (Amplified Luminescent Proximity Homogeneous Assay Screen) measurements. AlphaScreen measurement as well as photochemical measurement technology and LOCI (Luminescent Oxygen Channeling Immunoassay) are described for example in U.S. Pat. No. 6,406,913 to Ullman et al.

The microplate reader 10 can be used for analyzing samples arranged in the wells 2 of a microplate 1. Microplates 1 used in absorbance-based assays are typically clear. In luminescence- or fluorescence-based assays opaque plates are also often used to minimize cross talk between samples and to enhance signal strength. The microplate reader 10 is configured to measure electromagnetic radiation transmitted or emitted by the samples arranged in the microplate 1. For instance, the microplate reader 10 can be configured to determine absorbance values of the samples. The microplate reader 10 comprises illuminating means 11, which are capable of producing electromagnetic radiation with a specific wavelength or wavelength range. The electromagnetic radiation can be visible light (wavelength range approximately 380-750 nm), ultraviolet light (10-380 nm) or infrared light (750 nm-1 mm). The illuminating means 11 are configured to illuminate the samples in the wells 2 of the microplate 1. The illuminating means 11 are not necessarily an essential part of the microplate reader 10. For instance, if the microplate reader 10 is used for measuring chemiluminescence, such as bioluminescence, the illuminating means 11 are not needed.

The microplate reader 10 further comprises detection means 13. The detection means 13 are configured to measure electromagnetic radiation transmitted or emitted by the samples. In the case of absorbance measurements, the detection means 13 are configured to measure the radiant flux transmitted through the samples in the wells 2 of the microplate 1. In other kinds of measurements, such as in fluorescence or luminescence measurements, the detection means 13 can measure electromagnetic radiation emitted by the samples. The microplate reader 10 can comprise two or more different detection means 13 for different measurements.

The microplate reader 10 is controlled via input means 14. The input means 14 can comprise, for instance, operating buttons, a keyboard and/or a touch display. Via the input means 14, the user of the microplate reader 10 can control the operation of the microplate reader 10, adjust parameters, and/or change settings of the microplate reader 10. The results of the analysis can be displayed on a display 12. The display 12 can be an integral part of the microplate reader 10 or an external display connected to the microplate reader 10. The input means 14, illuminating means 11, detection means 13 and display 12 communicate with a central processing unit (CPU) 15. The input means 14 and the display 12 do not need to be connected directly to the CPU 15. The microplate reader 10 could also be controlled via software that is installed on an external general-purpose computer, such as a PC. The input means 14 could thus comprise for example a keyboard that is connected to the external computer. Also the display 12 could be connected to the external computer. All the connections may be implemented by wire or by any wireless means and the external computer may be a remote server or a cloud server.

Figure 3:
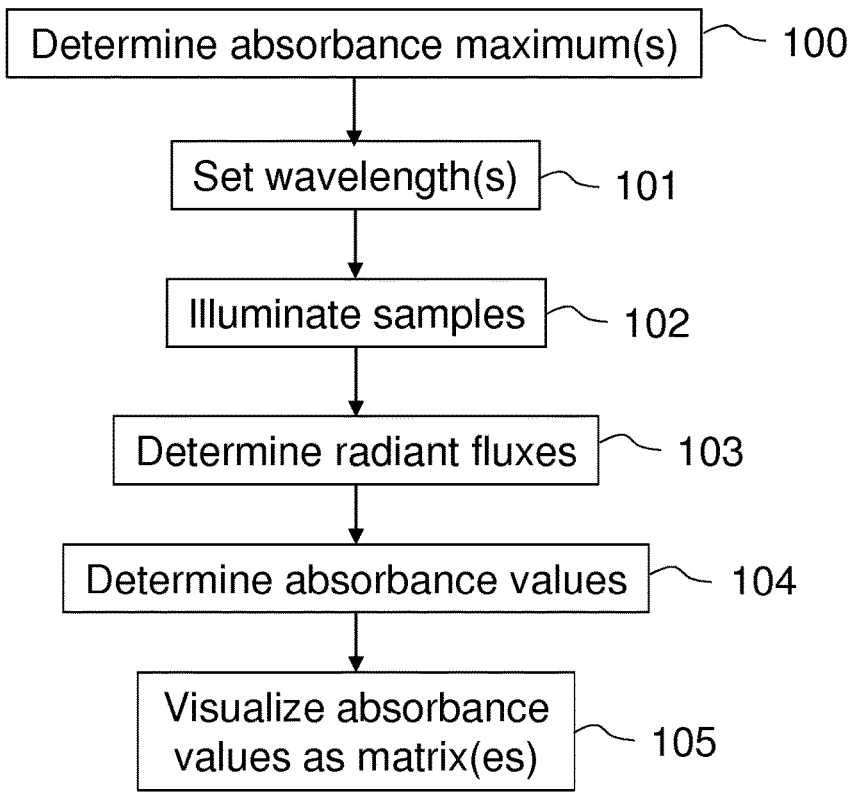
FIG. 3 shows as a flowchart an example of the operation of a microplate reader.

An example of the operation of the microplate reader 10 is shown as a flowchart in FIG. 3. In the example of FIG. 3, the microplate reader 10 is used for absorbance measurement. In a first step of the operation, a desired wavelength is set 101. The set wavelength is used in a second step of the operation for illuminating samples placed in the wells 2 of a microplate 1 102. The user can select the desired wavelength via the input means 14. Typically an exact wavelength is selected by the user, but in practice the microplate reader 10 is capable of producing electromagnetic radiation with a certain bandwidth. A narrow bandwidth is usually preferred. The acceptable bandwidth depends on the application. In some cases, a bandwidth of 20 nm is sufficient. In some applications, the bandwidth should be at most 10 nm. In some applications, the bandwidth should not exceed 2.5 nm.

In absorbance and fluorescence measurements, the selection of the wavelength that is used for illuminating the samples is usually based on the wavelength at which an absorbance maximum takes place. The expression "absorbance maximum" refers to a wavelength of electromagnetic radiation, at which there is a peak in the absorbance values, i.e. at which wavelength less radiation is passed through the samples than at the adjacent wavelengths. The samples can have several local absorbance maximums. For instance, local absorbance maximums can be found in the wavelength ranges of ultraviolet light, visible light and infrared light. It is also possible that there are several local absorbance maximums in the wavelength range of visible light. The selected wavelength typically corresponds to a local absorbance maximum or is at least close to the local absorbance maximum. For instance, the selected wavelength can be within 20 nm of the local absorbance maximum. According to one example, the selected wavelength is within 10 nm of the local absorbance maximum. According to another example, the selected wavelength is within 2.5 nm of the local absorbance maximum. If a certain wavelength range for illuminating the samples is selected, the wavelength range preferably envelops the local absorbance maximum. Typically the user knows where a local absorbance maximum takes place and the desired wavelength or wavelength range can be set by the user. The microplate reader 10 can also be configured to determine the absorbance maximum. The results are typically shown as an absorbance curve, which shows the amount of absorbance as a function of wavelength. The user may then select the suitable wavelength based on the results presented by the instrument. Alternatively, the microplate reader 10 can suggest a certain wavelength, which can then be confirmed by the user.

In the example of FIG. 3, the method comprises a preliminary step 100, in which a local absorbance maximum of the samples is determined. However, this step is not necessary, but often the absorbance maximums are known, in which case the user can set the wavelength for the absorbance measurements based on prior knowledge.

In the second step of the operation, the samples placed in the wells 2 of the microplate 1 are illuminated with electromagnetic radiation having a specific wavelength or wavelength range 102.

In a third step of the operation, the detection means 13 are used for determining radiant fluxes transmitted through the samples 103.

In a fourth step of the operation, absorbance values of the samples are determined 104. The absorbance of a material is commonly defined to be the common logarithm of the ratio of incident to transmitted radiant power through the material. The absorbance can thus be expressed by the following equation:

$$A = \log_{10}(P_0/P) \quad (1),$$

where
$P_0$ is the radiant flux received by the sample, and
P is the radiant flux transmitted by the sample.

The absorbance is dimensionless.

The absorbance values are determined for a certain wavelength of electromagnetic radiation. The wavelength used is typically the wavelength where a local absorption maximum of the sample is known to take place. If the wavelength of the absorption maximum is known, the wavelength or wavelength range used for illuminating the samples can be selected by the user. Alternatively, the microplate reader 10 can be used for carrying out a spectral analysis that determines the absorbance values over the whole operating range or part of the operating range of the microplate reader 10. The measured absorbance values can correlate to the amount of certain cellular metabolites or certain biological functions, such as cellular respiration, membrane integrity, or the activity of a specific enzyme (i.e. lactase dehydrogenase) or other proteins present in the sample.

In a fifth step of the operation, the determined absorbance values are visualized as a matrix 105. The results of the analysis are shown on the display 12.

In case the samples have several local absorbance maximums, the absorbance measurements can be carried out using several set wavelengths. Consequently, several result matrixes are formed for displaying the results.

The operation of the microplate reader 10 in other types of measurements is similar to the operation described above. Fluorescent measurement is shown as a flowchart in FIG. 8. In fluorescent measurements, the illuminating means 11 are used as an excitation source. A specific wavelength is set 301, the samples are illuminated using electromagnetic radiation with a narrow bandwidth around the set wavelength 302, and the electromagnetic radiation emitted by the samples is measured using the detection means 13 303. The measured values are visualized as a matrix 304.

In fluorescence measurements, the electromagnetic radiation emitted by the samples may be directed through a wavelength filter before being measured. The wavelength filter isolates emitted photons from excitation photons. There may be several fluorophores present in one sample. Several measurements can thus be carried out and the results of each measurement can be displayed as a separate matrix. The user may then choose which matrix is shown on the user interface display. Also several matrixes may be displayed simultaneously.

Figure 4:
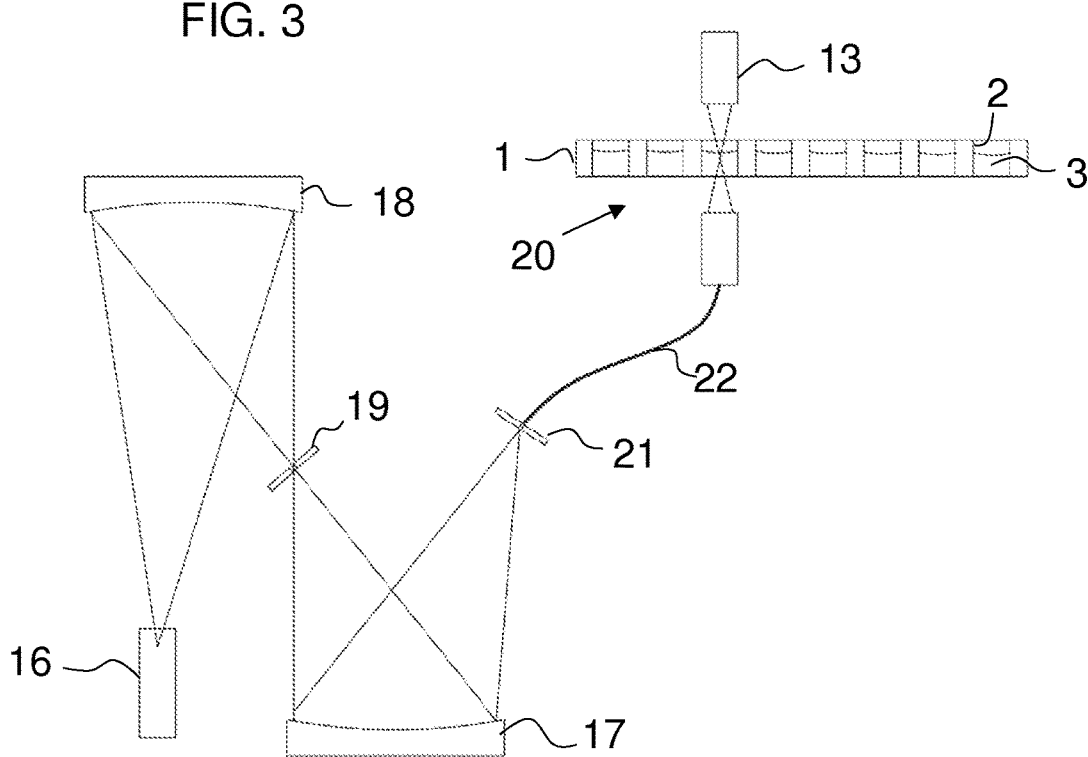
FIG. 4 shows a schematic view of a spectrophotometer.

FIG. 4 shows in more detail an example of a microplate reader 10, which is configured for absorbance measurements. In the example of FIG. 4, the illuminating means 11 comprise a light source 16. The light source 16 can be, for instance, a Xenon flash lamp. The light source 16 could also be, for instance, a quartz-halogen lamp. The light source 16 produces electromagnetic radiation, such as visible light (wavelength range approximately 380-750 nm), ultraviolet light (10-380 nm) or infrared light (750 nm-1 mm) with a broad spectrum. For selecting a specific wavelength, the illuminating means 11 further comprise a monochromator 17. The monochromator 17 produces a light beam with a narrow bandwidth. According to one example, the bandwidth of the light after the monochromator 17 is less than 2.5 nm. However, in some applications also a broader bandwidth is sufficient. Instead of a monochromator, also an interference filter could be used as means for wavelength selection. The light source could also be a narrow band light source, such as a LED or a laser. In that case, a monochromator, interference filter or other external means for wavelength selection may not be needed.

The light beam from the light source 16 is transmitted via optics of the microplate reader 10 to the monochromator 17. In the example of FIG. 4, the optics between the light source 16 and the monochromator 12 comprises a mirror 18 and an entrance slit 19. However, the optics of the microplate reader 10 can be constructed in many different ways.

In the example of FIG. 4, the light is transmitted from the monochromator 17 to a reading station 20 via an exit slit 21 and an optical fiber 22. The light is passed through the samples 3 that are placed in the wells 2 of the microplate 1. The intensity of the light that is passed through the samples 3 is measured by means of a detector 13, such as a silicon photodiode or a photomultiplier tube. In the example of FIG. 4, the detector 13 is moved from one sample 3 to another. However, the microplate reader 10 could comprise several detectors 13 for allowing several samples 3 to be measured simultaneously.

If the microplate reader 10 was used for other kinds of measurements, the illuminating means 11 and the detection means 13 could be configured differently. For instance, in fluorescence measurements the detection means 13 would be configured to measure electromagnetic radiation emitted by the samples when excited by the illuminating means 11. Also, usually emission filters, such as lowpass or bandpass emission filters, are required before detector to filter out background fluorescence or to isolate fluorescence signals originating from multiple fluorophores in one sample. A wavelength filter can also be needed for isolating emitted photons from excitation photons.

Figure 5B:
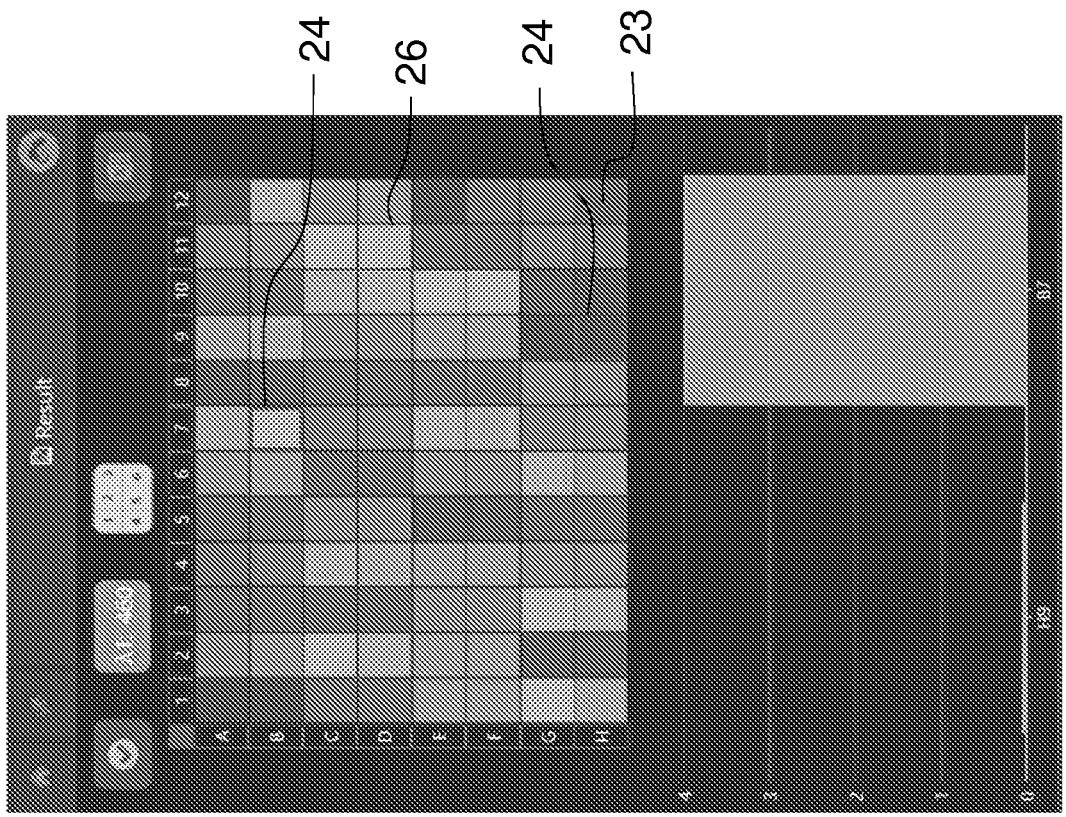
FIGS. 5a and 5b show examples of result matrixes.
Figure 5A:
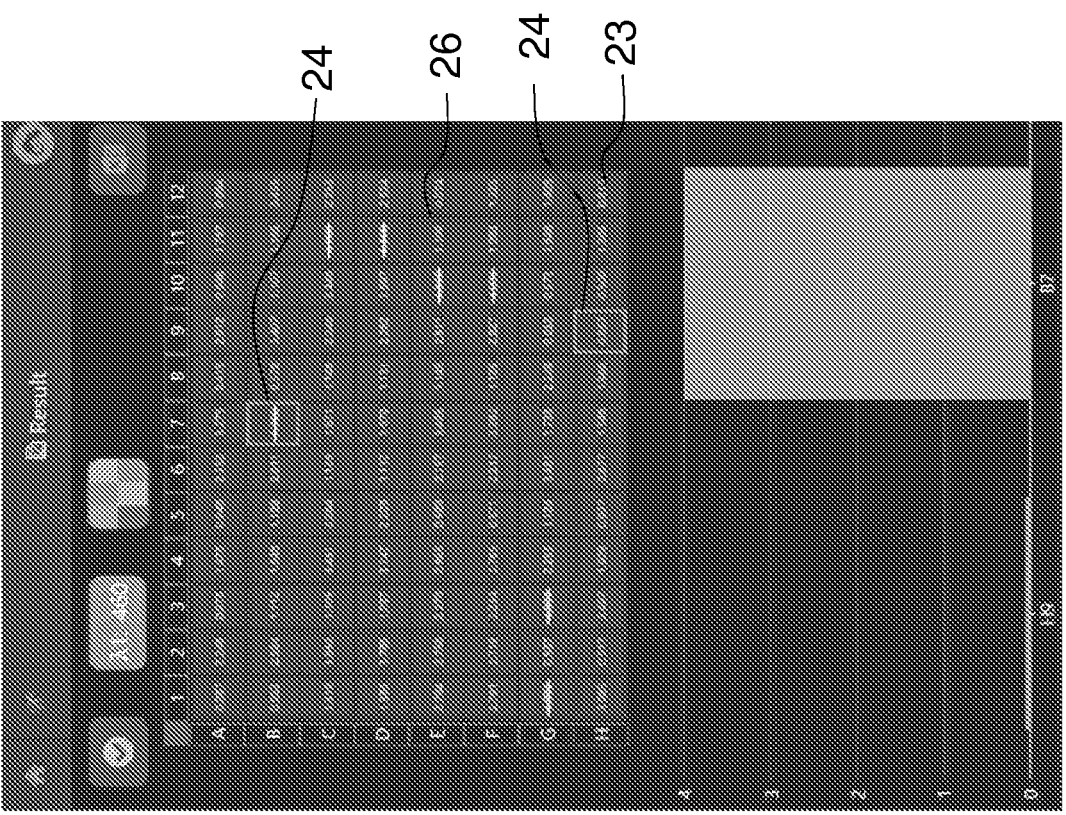
Figure 5C:
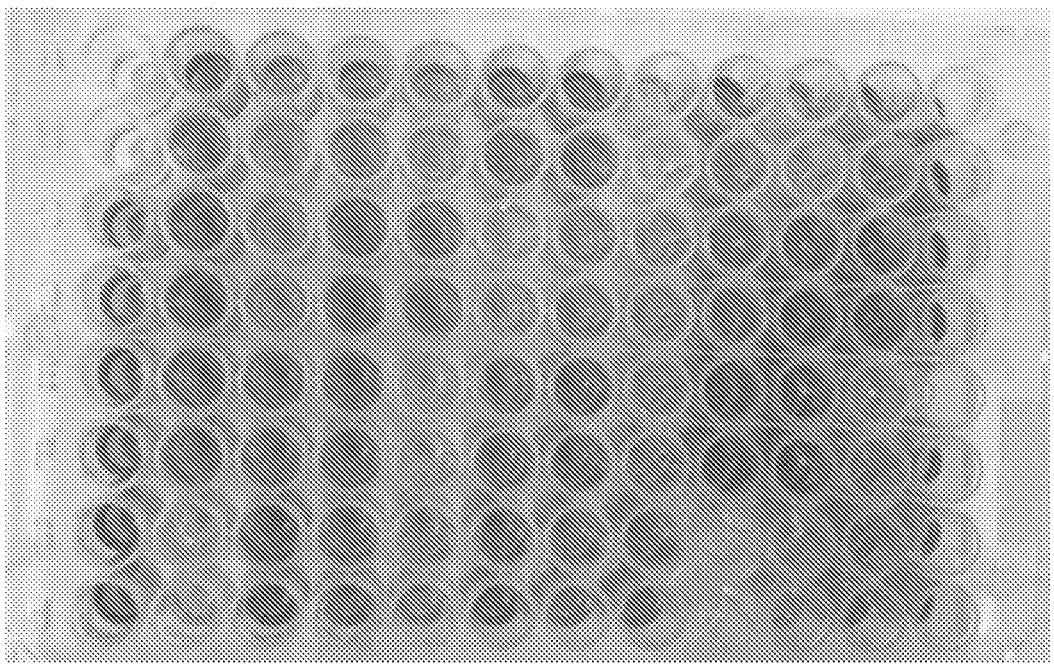
FIG. 5c shows a microplate corresponding to the result matrixes of FIGS. 5a and 5b.

FIGS. 5a and 5b show examples of result views of the microplate reader 10. FIG. 5c shows a corresponding microplate 1. In the examples of FIGS. 5a and 5b the microplate reader 10 has been used for absorbance measurements. FIG. 5a shows a result view where the absorbance values are shown as numerical values, which typically fall in the range between 0 and 4. The absorbance values are shown on the display 12 as a matrix which comprises a number of cells 23. Each cell 23 of the matrix corresponds to a well 2 of the microplate 1. Since the number of wells 2 of a microplate 1 and the corresponding number of cells 23 in the matrix is large, it may be difficult to quickly detect the absorbance values of interest, for example low and high values. Therefore, the cells 23 with the highest and lowest absorbance values are automatically highlighted by surrounding the cells 23 with a frame 24. The result matrix would be similar in case of other kinds of measurements. For instance, in the case of fluorescence measurements, values corresponding to the radiation emitted by the samples would be shown instead of the absorbance values.

For allowing the user to quickly detect those cells 23 that show particularly low or high measured values, the data can also be visualized using a heat map, where the individual values are presented as colors. FIG. 5b shows an example of a heat map. The user of the microplate reader 10 can switch between the different views or choose to show them simultaneously.

Figure 13B:
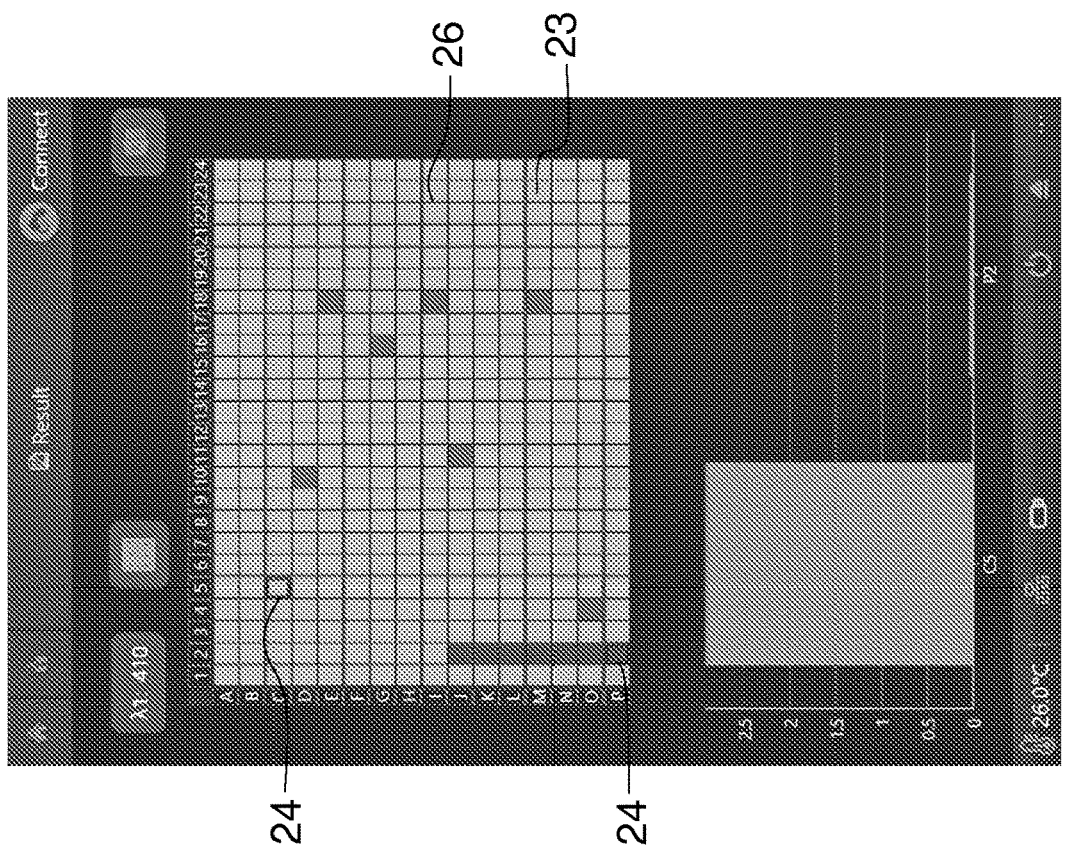
FIGS. 13a and 13b show further examples of result matrixes.
Figure 13A:
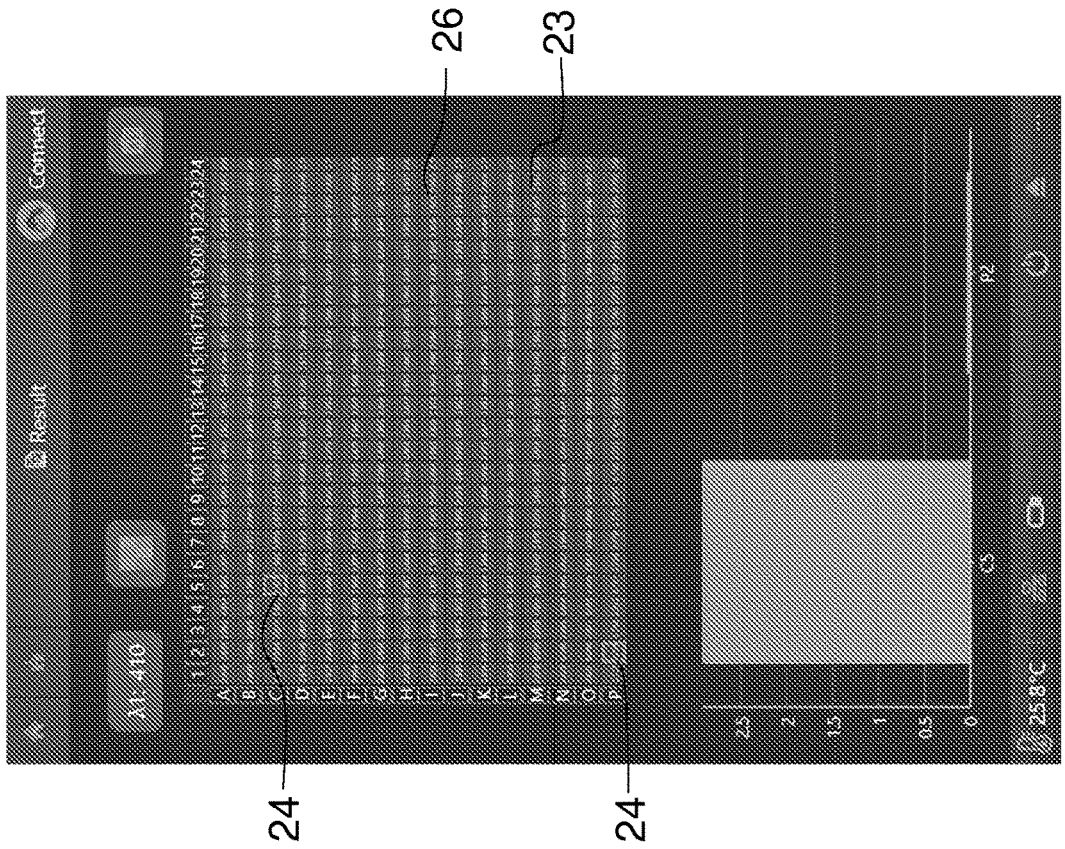

The result views of FIGS. 13a and 13b are similar to the views of FIGS. 5a and 5b. However, in this case the microplate 1 comprises 384 wells 2. Also in the examples of FIGS. 13a and 13b, the cells 23 with the highest and lowest absorbance values are automatically highlighted by surrounding the cells 23 with a frame 24. The difference between the numerical view of FIG. 13a and the heat map view of FIG. 13b clearly shows benefits of the invention. In the numerical view, the user can hardly distinguish anything. In the heat map view, the user can immediately see whether the assay has worked as expected. In this example, cells A2 to I2 are positive controls and cells J2 to P2 are negative controls. The colors of those cells show that the assay has worked properly. The user can also identify hits that are sufficiently different from the positive controls. The hits are shown with a different color and can be chosen for follow-up studies. An additional data analysis is not needed. The method and the analyzing device according to the invention thus improve the reliability and speed of the analysis.

The measured values, such as the absorbance values of the samples, 3 are visualized by the color intensity of the cells 23. The color intensity or actually the transparency or translucency of each cell 23 is thus determined on the basis of the measured value of the respective sample 3. In computer graphics changing the transparency of a color without affecting its hue is generally accomplished by alpha blending. It is a process that blends the foreground color with the background color which in this case is preferably black. The blended color is computed as a weighted average of the foreground and background colors and the foreground color has a value from 1 to 0.1. The alpha channel values, i.e. the values of the foreground color of the cells 23 have a positive correlation with the measured values. The higher the measured value of a cell 23 is, the higher alpha channel value it receives. The samples 3 with low absorbance or other measured values are thus shown in the result matrix as more transparent (less intensely colored) cells 23 than the samples 3 with high absorbance or other measured values.

When using RGB color space, reducing the saturation of the sample 3 color would ultimately lead to the color hue tint changing towards white, black or gray, depending on the color. This is because in RGB mode, which is an additive color mode, the hue of a color is affected by the individual values of the red, green and blue channels. In alpha blending the actual amount of the R, G and B values is not changed so the hue of the color is not affected.

Figure 7:
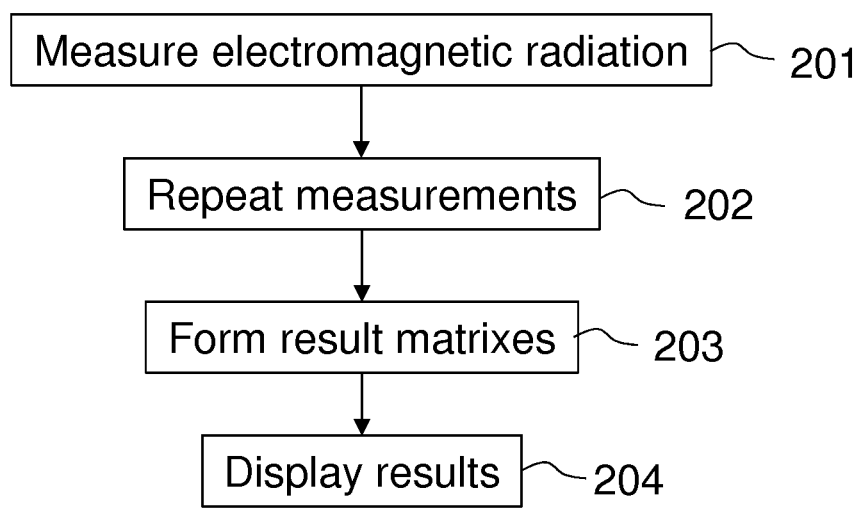
FIG. 7 shows the method according to the invention as a flowchart.

The method according to the invention is shown as a flowchart in FIG. 7. In a first step of the method, electromagnetic radiation emitted or transmitted by the samples 3 arranged in the wells 2 of a microplate 1, or in some other kind of sample receptacles of a platform that is adapted to accommodate a plurality of separate samples, is measured 201. Instead of a standard microplate 1, the platform could be, for instance, a PCR array. In a second step, the measurement step 201 described above is repeated at predetermined time intervals 202. The number of the measurements depends on the assay. The measurements can be repeated a predetermined number of times at predetermined time intervals. Alternatively, the measurements can be continued over a predetermined period of time. It is also possible that the number of measurements or the duration of the analysis is not fixed but the number of measurements or the duration of the analysis is determined on the basis of the measurement results. For instance, the measurements can be continued until the reactions in the samples 3 end or the reaction speed drops below a certain limit value. The period of time between two consecutive measurements does not need to be constant. For instance, the reaction speed of a chemical or a biological process can be faster at the beginning of the process, and the measurement can be repeated at shorter time intervals at the beginning of the process.

In a third step of the method, result matrixes are formed 203. Each result matrix is formed in the manner described above in connection with the description of single measurements. A result matrix thus comprises a plurality of cells 23, each cell 23 corresponding to a well 2 of the microplate 1 or a sample receptacle of some other kind of platform. The measurement value of each sample 3 is used as an input for determining the visual properties of the respective cell 23 in the result matrix. For instance, the transparency of the cell can be determined on the basis of the measured value, such as the absorbance or fluorescence value. The result matrix can additionally be provided with a time stamp. In a fourth step of operation, the results are displayed as consecutive matrixes in respect of time 204. The results can thus be presented as an animation, where color changes of individual samples 3 or cells are clearly illustrated.

The steps of the method do not need to take place in the order shown in FIG. 7. For instance, the results can be displayed in real-time, in which case a result matrix is formed and displayed after each measurement step. Instead of or in addition to displaying the results in real-time, the results can be saved in a memory. The results can be stored in a memory of a microplate reader 10 or other analyzing device, and/or on an external computer. The external computer can be a remote server or a cloud server.

The results can be saved as a raw data, which is then used for forming the result matrixes. Alternatively or in addition to that, a result matrix can be formed after each measurement and the result matrixes can be stored in an image format. The measurement values can also be used as an input for creating a video file illustrating the change of the measurement values between consecutive measurements. Video files can be stored in a memory of a microplate reader 10 or other analyzing device, and/or on an external computer. The external computer can be a remote server or a cloud server. The video files can be played both offline and online. This embodiment would be especially useful also for combining heat maps from separate but connected experiments to a video format so that any changes in the sample results can be monitored directly visually.

The present invention is a clear improvement over the conventional way of displaying the results of kinetic assays as graphs, where the measured values of each cell are displayed as a curve as a function of time. In particular when the number of samples is more than a few, for example more than five, the behavior of individual samples in the conventional analyzing methods is difficult to interpret. With the present invention, the scientists utilizing kinetic studies can more easily interpret large amounts of data. The results can be shown in a readable format both in real-time and afterwards.

A particular embodiment of the invention can be applied when the method according to the invention is used for absorbance measurements in the wavelength range of visible light. The wavelength that has been set for the absorbance measurements can be used as a further input for determining the visual properties of the cells 23. The color of each cell 23 in the heat map can be selected so that the color corresponds to the color of the sample 3 as perceived by the human eye. The color of each cell 23 can thus be selected to be the complementary color of the color corresponding to the wavelength set for the absorbance measurements.

Figure 6:
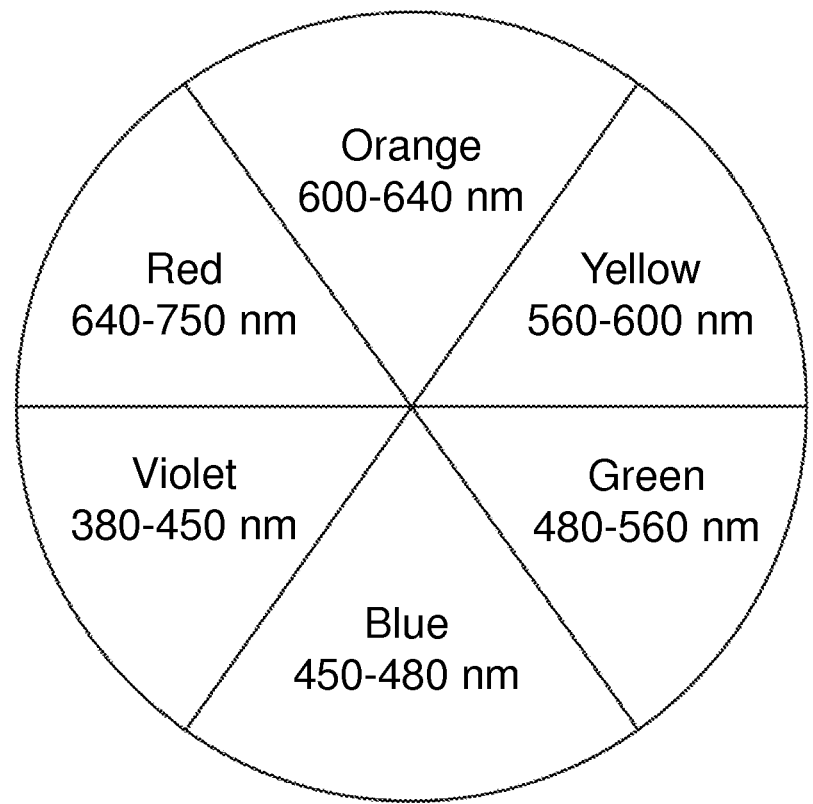
FIG. 6 shows a diagram for determining the colors used for visualizing measured absorbance values.

FIG. 6 shows an exemplary and simplified diagram illustrating the selection of the color of the cells. The diagram of FIG. 6 comprises six sectors, which represent different wavelength ranges of visible light (the main colors of a color wheel). When the microplate reader 10 is operated in the wavelength range of visible light, the wavelength set for the wavelength measurements 3 falls within one of the six ranges of FIG. 6. The set wavelength is typically close to a local absorbance maximum. The samples 3 thus absorb light with that wavelength. As a result, the color of the samples 3 as perceived by the user is thus the complementary color of the color corresponding to the wavelength set for the absorbance measurements. Complementary colors are located in the diagram of FIG. 6 in opposite sectors. The color used in the cells 23 of the matrix is thus selected from a sector that is located opposite to the sector comprising the wavelength that has been set for the absorbance measurements. As an example, if the set wavelength is 460 nm as shown in FIGS. 5a and 5b, i.e.

the light used for illuminating the samples 3 is blue, the cells 23 of the result matrix are shown as orange. In the method according to the invention, the result matrix reflects the visual color of the samples 3 as seen by naked eye. This makes reading of the results more intuitive to the users, who are used to handling colored samples, and also more reliable, because process errors can be spotted at the same time. According to an embodiment of the invention, the color space used is preferably RGB or ARGB, preferably comprising 8 bits in all three color channels with values of 0-255, but also other suitable numbers of colors and color profiles may be utilized.

In fluorescence measurements, the color of each cell 23 in the heat map can be selected so that the color corresponds to the color of the maximum emission wavelength of the fluorophore which is the wavelength detected by the detector or seen by a human eye.

By presenting the measurement results as consecutive matrixes and using the set wavelength as an input for selecting the color of the cells 23 of the matrixes, a realistic replica of the actual experiment can be created. Scientists who are accustomed to analyzing colored samples can thus easily interpret the measurement results. Similarly, presenting the measurement results as consecutive matrixes and using the detected wavelength as an input for selecting the color of the cells 23 of the matrixes help the user in interpreting the results.

In the examples of FIGS. 5a and 5b, two cells 23 of the result matrixes are bordered with a differently colored frame 24. The frames 24 are used for highlighting the cells 23 with the lowest and highest measured values and/or for indicating a selection of a cell 23 within the matrix. In case of absorbance measurements, the color of the frame 24 can be similar to the color that corresponds to the wavelength set for the absorbance measurements. The wavelength of the color can be for example within 20 nm of the wavelength set for the absorbance measurements. Preferably the color of the frame 24 corresponds to the set wavelength. The color of the frame 24 is thus the complementary color of the color of the cell 23, which makes the frame 24 easy to spot. The color of the borders 26 that are used for separating any unframed cells 23 from each other is any color other than the color of the frames 24 or the cells 23, for example black, white or dark grey. The same color is preferably used as a background color.

The color selection described above can be applied when the wavelength of the electromagnetic radiation is in the range of visible light. The absorbance or fluorescence measurements could also be done in the wavelength range of ultraviolet and/or infrared light. In case the wavelength of the electromagnetic radiation is in the wavelength range of ultraviolet or infrared light, the cells 23 can be shown in a predetermined color. The color of the cells 23 can be for example black or white. Also in other types of measurements, such as fluorescence or luminescence measurements, the cells 23 can be shown in a predetermined color. The color of the cells 23 could also be selected by the user.

Figure 10:
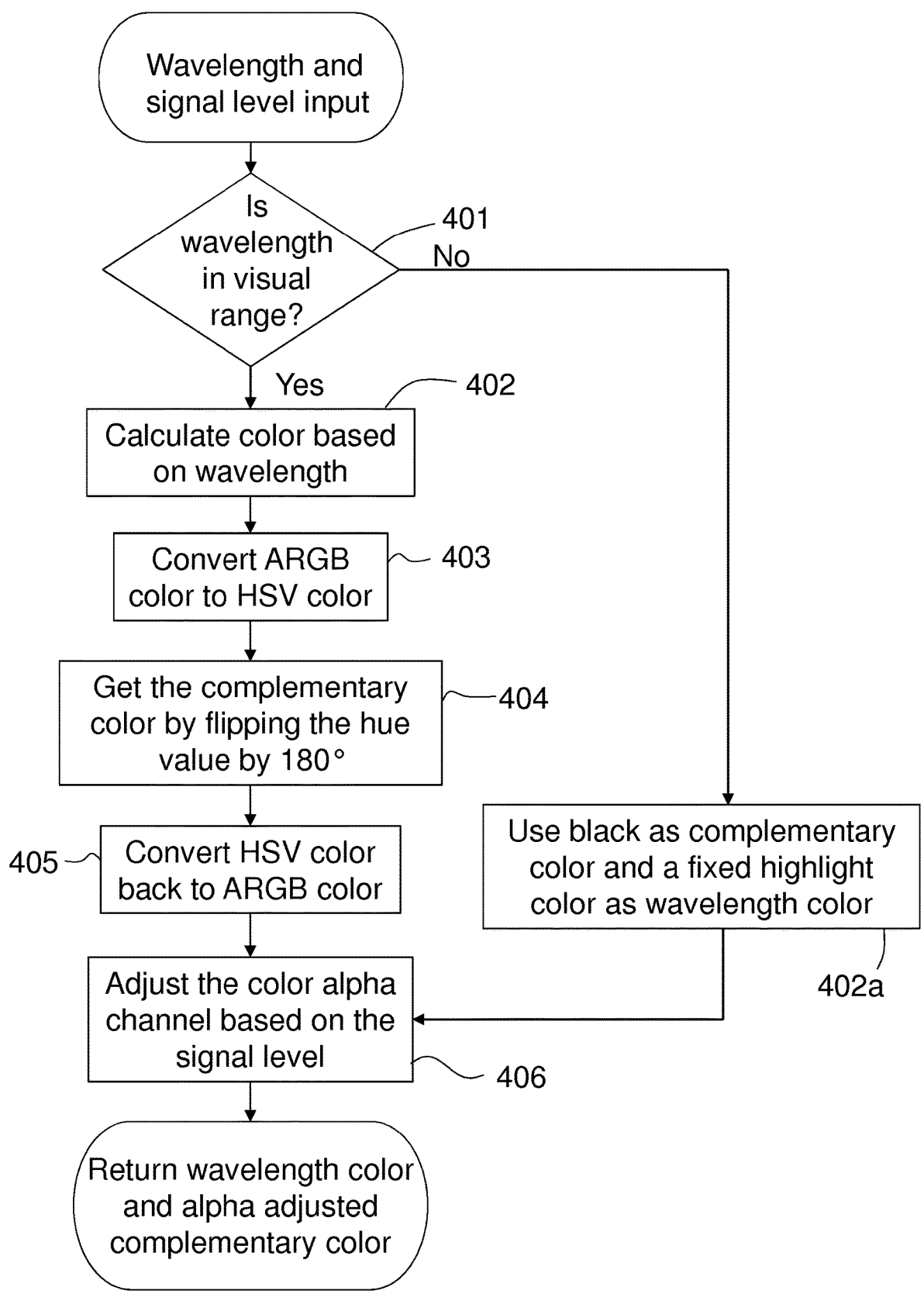
FIG. 10 shows as a flowchart an example of the steps for determining colors of a result matrix.

FIG. 10 shows as a flow chart an example of the steps for determining the visual properties of the cells 23 of a result matrix. In the example of FIG. 10, absorbance values of samples 3 are determined. A wavelength of the electromagnetic radiation used for illuminating the samples 3 is used as an input for the method. Another input is a signal level, which corresponds to an absorbance value of a sample. In a first step 401 of the method, it is determined whether the wavelength is in the wavelength range of visible light. If the wavelength is in the wavelength range of visible light, the color of the light is calculated based on the wavelength 402. In the next step, the calculated RGB or ARGB color is converted to an HSV color 403. In a fourth step, complementary color is determined by flipping the hue value of the HSV color by 180 degrees 404. The obtained HSV color is converted back to an ARGB color 405. The alpha channel of the color is adjusted based on the signal level 406. The method returns a wavelength color and an alpha adjusted complementary color. The wavelength color can be used as the color of a highlighting frame 24. In case the wavelength of the electromagnetic radiation used for illuminating the samples is outside the wavelength range of visible light, the steps 402-405 for determining the complementary color are omitted. Instead, black is used as a complementary color and a predetermined highlight color is used as the wavelength color 402a.

Figure 11:
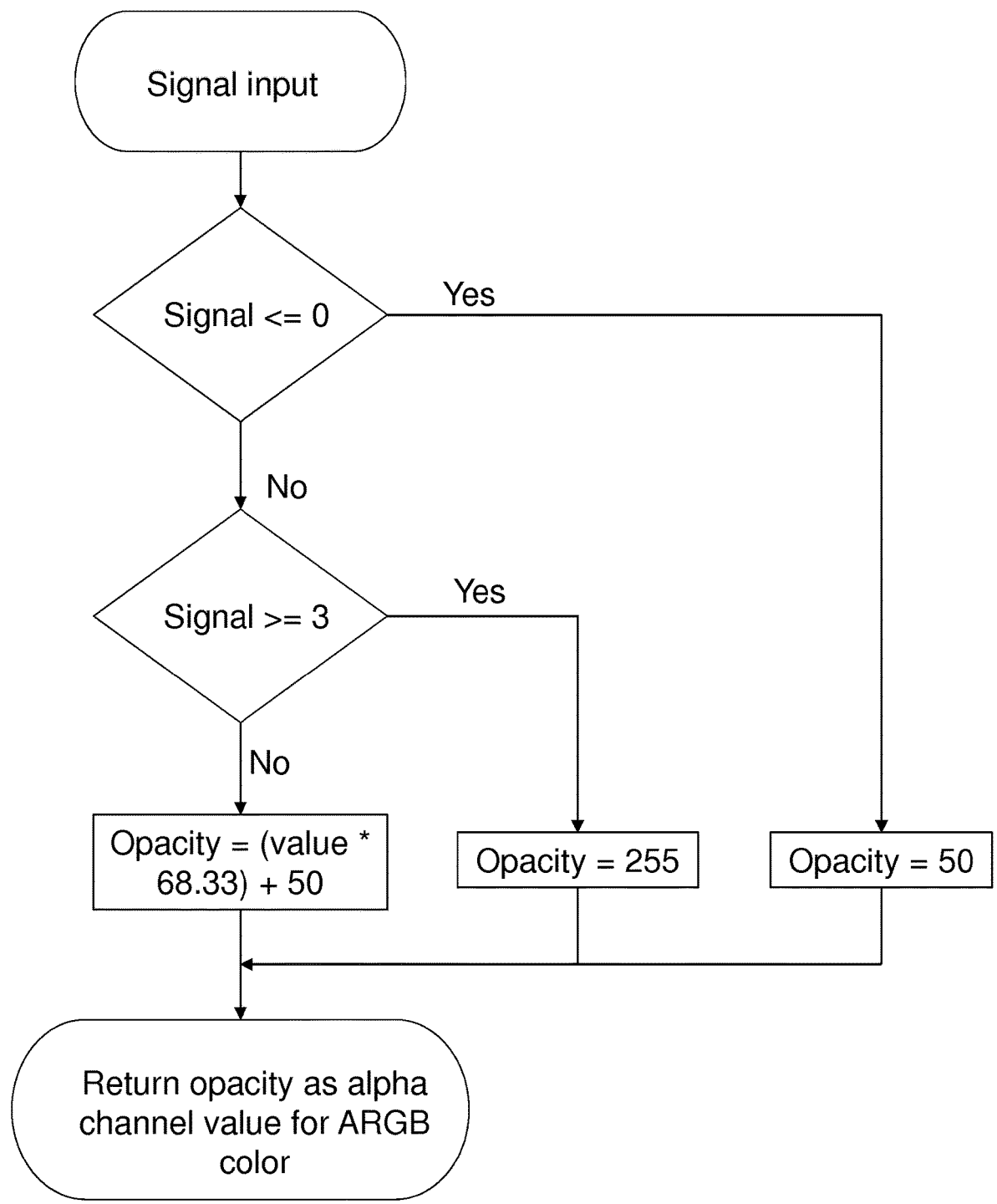
FIG. 11 shows an example of the steps for determining transparencies of the cells of a result matrix.

FIG. 11 shows an example of the steps of determining the transparency or opacity of the cells 23 of a result matrix. In the example of FIG. 11, if the value of the signal, which is in the case of absorbance measurements the absorbance value, is below zero, an opacity value of 50 is given to the cell 23. If the signal is above 3, an opacity value of 255 is given to the cell 23. For signal values between 0 and 3, the opacity value is calculated by equation opacity=signal value*68.33+50.

Figure 12:
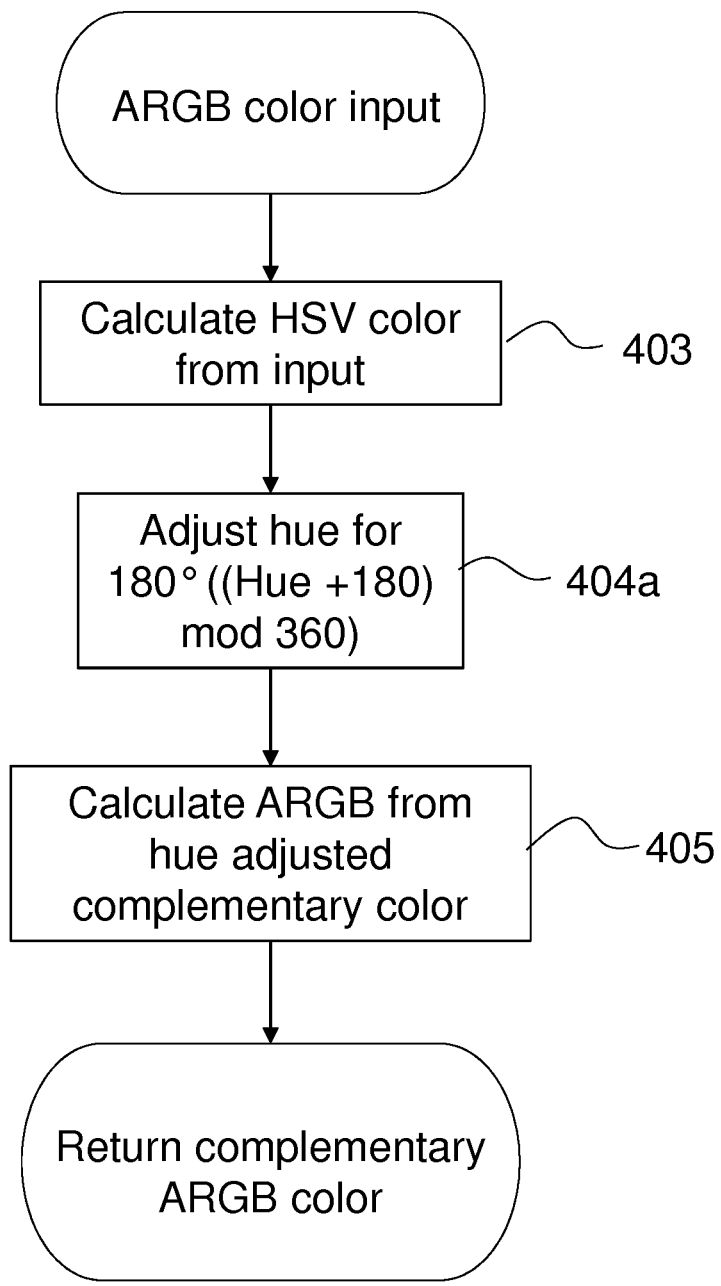
FIG. 12 shows the steps of determining the complementary color for a color having hue of 180°.

FIG. 12 shows a modified version of part of the method of FIG. 10. If the hue of the HSV color used as an input for determining the complementary color is 180, the step 404 of determining the complementary color is modified. In the modified step 404a the hue value is adjusted by 180 degrees and then modulo operation is performed on the adjusted value.

The present invention could also be applied to a nucleic acid analyzer instrument such as an instrument used for amplifying sample nucleic acids by Polymerase Chain Reaction (PCR) or a DNA sequencer.

Figure 8:
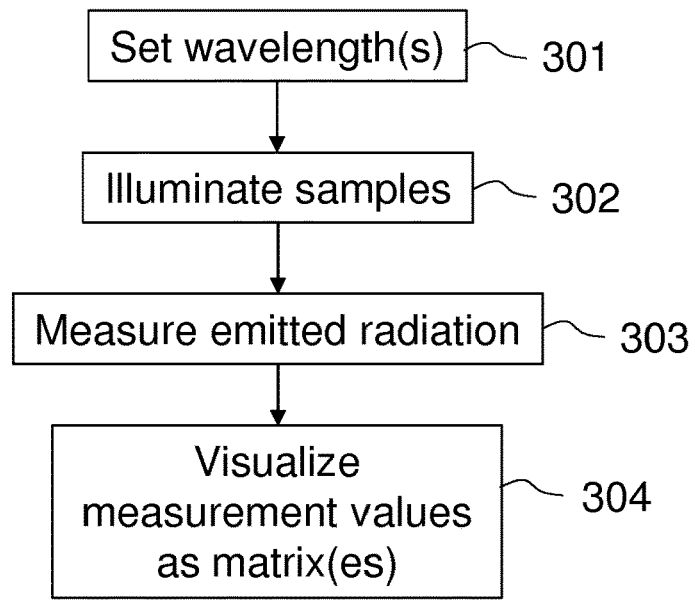
FIG. 8 shows as a flowchart another example of the operation of a microplate reader.

When the method of is applied to PCR analysis, the process is very similar to the fluorescence measurement shown in FIG. 8. The main components of a PCR analyzer are the same as shown in FIG. 2. The illuminating means 11 are used as an energy source. The illuminating means 11 can comprise a light source, such as a lamp, laser or LED. The light from the light source can be passed through a filter. The light is directed at the samples. The samples can be arranged in liquid containing receptacles or cavities in an array or microplate format. The light emitted by the samples is measured by detection means 13. The emitted light can be passed through a filter before being measured.

Figure 9:
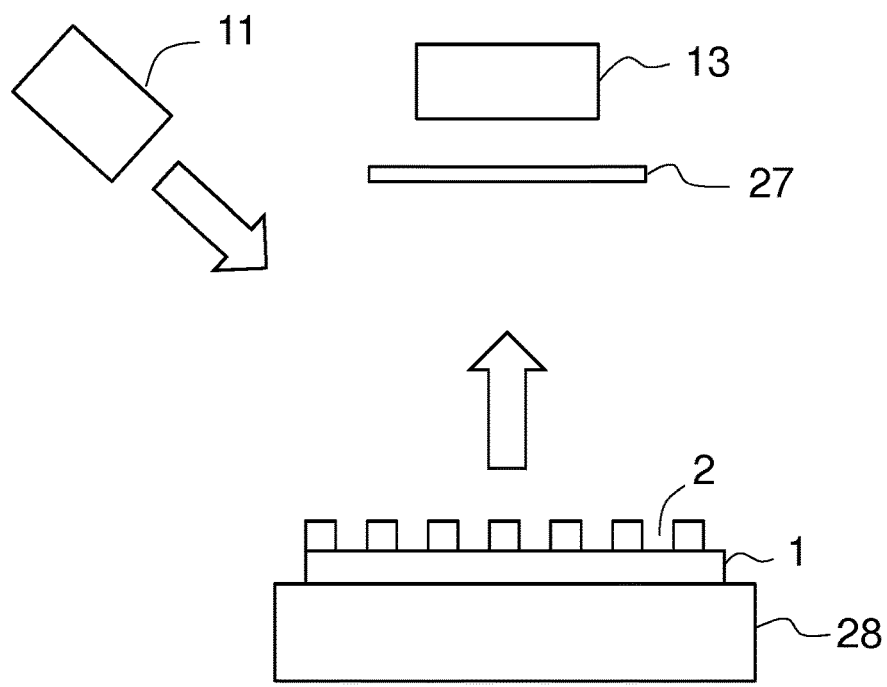
FIG. 9 shows schematically an arrangement for PCR monitoring.

FIG. 9 shows schematically an arrangement for PCR monitoring. The samples to be analyzed are placed in sample receptacles 2 of a suitable platform 1. A heat source, such as a heating block 28 is used for heating the samples. Electromagnetic radiation is directed at the samples by a light source 11. The light source 11 can be, for instance, a lamp, laser or LED. Because of the excitation by the light source, the samples emit light. The light emitted by the samples is passed through a filter 27 and monitored by a detector 13.

It will be appreciated by a person skilled in the art that the invention is not limited to the embodiments described above, but may vary within the scope of the appended claims.

The invention claimed is:

1. A method of analyzing one or more samples arranged in sample receptacles of a platform that is configured to hold a plurality of separate samples, the method comprising the steps of:

illuminating the samples using electromagnetic radiation, obtaining an electromagnetic radiation measurement for each respective sample of the one or more samples, wherein the electromagnetic radiation measurement for each respective sample of the one or more samples measures electromagnetic radiation transmitted or emitted by the respective sample, repeating the obtaining of electromagnetic radiation measurements for each respective sample of the one or more samples a plurality of times at predetermined intervals, on the basis of each electromagnetic radiation measurement measuring electromagnetic radiation transmitted or emitted by each respective sample, forming a result matrix comprising a plurality of cells, each cell of the result matrix corresponding to a sample receptacle of the platform, wherein an electromagnetic radiation measurement value of each sample is used as an input for determining visual properties of the respective cell in the result matrix, the visual properties including a color and a transparency of the cell, the transparency of each cell being determined on the basis of a measurement value of the respective sample and the color of each cell being determined based on a wavelength of the radiation emitted by the samples or based on a wavelength of the radiation used for illuminating the samples, and displaying the results as consecutive matrixes in respect of time.

2. The method according to claim 1, wherein the electromagnetic radiation measurement value of each sample comprises an absorbance value.

3. The method according to claim 2, wherein the samples are illuminated using electromagnetic radiation having a bandwidth of at most 20 nm around a set wavelength falling within the wavelength range of 380 nm-750 nm.

4. The method according to claim 3, wherein the set wavelength is used for determining the color of the cells.

5. The method according to claim 4, wherein the color of each cell is selected to be a complementary color of a color corresponding to the set wavelength.

6. The method according to claim 1, wherein the electromagnetic radiation measurement value of each sample comprises a luminescence value.

7. The method according to claim 6, wherein the wavelength of the electromagnetic radiation emitted by the samples is used for determining the color of each cells.

8. The method according to claim 7, wherein the color of each cell is selected so that the wavelength corresponding to the color is within 20 nm from the wavelength of the electromagnetic radiation emitted by the samples.

9. The method according to claim 1, wherein the electromagnetic radiation measurement value of each sample comprises a fluorescence value.

10. The method according to claim 1, wherein polymerase chain reaction (PCR) of the samples is monitored.

11. The method according to claim 1, wherein the color of each cell is selected so that the color corresponds to the color of the sample as perceived by the human eye.

12. The method according to claim 1, wherein the transparencies of the cells are set by means of alpha blending, and wherein alpha channel values of the cells have a positive correlation with the electromagnetic radiation measurement values.

13. The method according to claim 1, wherein the electromagnetic radiation measurement values are used for creating a video file illustrating a change of the electromagnetic radiation measurement values between consecutive electromagnetic radiation measurements.

14. The method according to claim 1, wherein the platform is a microplate and the sample receptacles are wells of the microplate.

15. An analyzing device comprising a detector, one or more processors, and a display, the analyzing device being configured to:

illuminate, using electromagnetic radiation, each respective sample of one or more samples arranged in one or more sample receptacles of a platform that is configured to hold a plurality of separate samples, obtain, via the detector an electromagnetic radiation measurement for each respective sample of the one or more samples, wherein the electromagnetic radiation measurement for each respective sample of the one or more samples measures electromagnetic radiation transmitted or emitted by the respective sample, repeat the obtaining of electromagnetic radiation measurements, via the detector, for each respective sample of the one or more samples a plurality of times at predetermined intervals, via the one or more processors, on the basis of each electromagnetic radiation measurement measuring electromagnetic radiation transmitted or emitted by each respective sample, form a result matrix comprising a plurality of cells, each cell of the result matrix corresponding to a sample receptacle of the platform, wherein an electromagnetic radiation measurement value of each sample is used as an input for determining visual properties of the respective cell in the result matrix, the visual properties including a color and a transparency of the cell, the transparency of each cell being determined on the basis of a measurement value of the respective sample and the color of each cell being determined based on a wavelength of the radiation emitted by the samples or based on a wavelength of the radiation used for illuminating the samples, and display the results on the display as consecutive matrixes in respect of time.

16. One or more processors for operating an analyzing device, the one or more processors being configured to execute instructions which cause the analyzing device to:

illuminate, using electromagnetic radiation, each respective sample of one or more samples arranged in one or more sample receptacles of a platform that is configured to hold a plurality of separate samples, obtain an electromagnetic radiation measurement for each respective sample of the one or more samples, wherein the electromagnetic radiation measurement for each respective sample of the one or more samples measures electromagnetic radiation transmitted or emitted by the respective sample, repeat the obtaining of electromagnetic radiation measurements for each respective sample of the one or more samples a plurality of times at predetermined intervals, on the basis of each electromagnetic radiation measurement measuring electromagnetic radiation transmitted or emitted by each respective sample, form a result matrix comprising a plurality of cells, each cell of the result matrix corresponding to a sample receptacle of the platform, wherein an electromagnetic radiation measurement value of each sample is used as an input for determining visual properties of the respective cell in the result matrix, the visual properties including a color and a transparency of the cell, the transparency of each cell being determined on the basis of a measurement value of the respective sample and the color of each cell being determined based on a wavelength of the radiation emitted by the samples or based on a wavelength of the radiation used for illuminating the samples, and display the results as consecutive matrixes in respect of time.

17. A method of analyzing one or more samples arranged in sample receptacles of a platform that is configured to hold a plurality of separate samples, the method comprising the steps of:

obtaining an electromagnetic radiation measurement for each respective sample of one or more samples arranged in one or more sample receptacles of a platform that is configured to hold a plurality of separate samples, wherein the electromagnetic radiation measurement for each respective sample of the one or more samples measures electromagnetic radiation emitted by the respective sample, repeating the obtaining of electromagnetic radiation measurements for each respective sample of the one or more samples a plurality of times at predetermined intervals, on the basis of each electromagnetic radiation measurement measuring electromagnetic radiation emitted by each respective sample, forming a result matrix comprising a plurality of cells, each cell of the result matrix corresponding to a sample receptacle of the platform, wherein an electromagnetic radiation measurement value of each sample is used as an input for determining visual properties of the respective cell in the result matrix, the visual properties including a color and a transparency of the cell, the transparency of each cell being determined on the basis of a measurement value of the respective sample and the color of each cell being determined based on a wavelength of the radiation emitted by the samples, and displaying the results as consecutive matrixes in respect of time.

18. An analyzing device comprising a detector, one or more processors, and a display, the analyzing device being configured to:

obtain, via the detector an electromagnetic radiation measurement for each respective sample of one or more samples arranged in one or more sample receptacles of a platform that is configured to hold a plurality of separate samples, wherein the electromagnetic radiation measurement for each respective sample of the one or more samples measures electromagnetic radiation emitted by the respective sample, repeat the obtaining of electromagnetic radiation measurements, via the detector, for each respective sample of the one or more samples a plurality of times at predetermined intervals, via the one or more processors, on the basis of each electromagnetic radiation measurement measuring electromagnetic radiation emitted by each respective sample, form a result matrix comprising a plurality of cells, each cell of the result matrix corresponding to a sample receptacle of the platform, wherein an electromagnetic radiation measurement value of each sample is used as an input for determining visual properties of the respective cell in the result matrix, the visual properties including a color and a transparency of the cell, the transparency of each cell being determined on the basis of a measurement value of the respective sample and the color of each cell being determined based on a wavelength of the radiation emitted by the samples, and display the results on the display as consecutive matrixes in respect of time.

19. One or more processors for operating an analyzing device, the one or more processors being configured to execute instructions which cause the analyzing device to:

obtain an electromagnetic radiation measurement for each respective sample of one or more samples arranged in one or more sample receptacles of a platform that is configured to hold a plurality of separate samples, wherein the electromagnetic radiation measurement for each respective sample of the one or more samples measures electromagnetic radiation emitted by the respective sample, repeat the obtaining of electromagnetic radiation measurements for each respective sample of the one or more samples a plurality of times at predetermined intervals, on the basis of each electromagnetic radiation measurement measuring electromagnetic radiation emitted by each respective sample, form a result matrix comprising a plurality of cells, each cell of the result matrix corresponding to a sample receptacle of the platform, wherein an electromagnetic radiation measurement value of each sample is used as an input for determining visual properties of the respective cell in the result matrix, the visual properties including a color and a transparency of the cell, the transparency of each cell being determined on the basis of a measurement value of the respective sample and the color of each cell being determined based on a wavelength of the radiation emitted by the samples, and display the results as consecutive matrixes in respect of time.

* * * * *